| United States Patent [19] | [11] Patent Number: 5,066,663 |
| --- | --- |
| Hobbs | [45] Date of Patent: Nov. 19, 1991 |

[54] SUBSTITUTED-HETERO-CYCLOPENTA-NONES AND CYCLOPENTENONES AND DERIVATIVES THEREOF ACTING AT MUSCARINIC RECEPTORS

[75] Inventor: Sheila H. Hobbs, Dexter, Mich.

[73] Assignee: Warner-Lambert Company, Morris Plains, N.J.

[21] Appl. No.: 526,361

[22] Filed: May 21, 1990

[51] Int. Cl.$^5$ .................... A61K 31/44; C07D 405/02
[52] U.S. Cl. ................................. 514/326; 514/252; 514/256; 514/275; 514/304; 514/305; 514/314; 514/340; 514/342; 514/343; 514/365; 514/374; 514/394; 514/397; 514/406; 514/415; 544/238; 544/323; 544/335; 544/336; 546/125; 546/135; 546/152; 546/209; 546/283; 546/284; 546/280; 546/281; 548/204; 548/235; 548/327
[58] Field of Search ............. 546/209, 275, 280, 281; 514/340, 342, 343, 326; 548/229, 230

[56] References Cited

U.S. PATENT DOCUMENTS

| | | | |
| --- | --- | --- | --- |
| 3,646,024 | 2/1972 | Holdrege | 540/222 |
| 4,324,791 | 4/1982 | Welstead | 514/326 |
| 4,547,504 | 10/1985 | Fabre | 514/326 |
| 4,742,073 | 5/1988 | Bundgaard et al. | 548/243 |
| 4,767,759 | 8/1988 | Weber et al. | 514/255 |
| 4,897,489 | 1/1990 | Yoshioka et al. | 548/243 |
| 4,970,217 | 11/1990 | Prücher et al. | 546/209 |

OTHER PUBLICATIONS

Gonzales et al. Tetra Hedron Letters, vol. 30, No. 16 pp. 2145–2148 (1984).
Sauerberg et al. Chem. Abstr. vol. 110 Entry 231941p, (1989).

*Primary Examiner*—Donald G. Daus
*Attorney, Agent, or Firm*—Francis J. Tinney

[57] ABSTRACT

Substituted-hetero-cyclopentanones and cyclopentenones and derivatives thereof are described, as well as methods for the preparation and pharmaceutical compositions of same, which are useful as centrally acting muscarinic agents and are useful as analgesic agents for the treatment of pain, as sleep aids and as agents for treating the symptoms of senile dementia, Alzheimer's disease, Huntington's chorea, tardive dyskinesia, hyperkinesia, mania, or similar conditions of cerebral insufficiency characterized by decreased cerebral acetylcholine production or release.

6 Claims, No Drawings

SUBSTITUTED-HETERO-CYCLOPENTANONES AND CYCLOPENTENONES AND DERIVATIVES THEREOF ACTING AT MUSCARINIC RECEPTORS

BACKGROUND OF THE INVENTION

The present invention relates to novel substituted hetero-cyclopentanones and cyclopentenones and derivatives thereof useful as pharmaceutical agents, to methods for their production, to pharmaceutical compositions which include these compounds and a pharmaceutically acceptable carrier, and to pharmaceutical methods of treatment. More particularly, the novel compounds of the present invention act at muscarinic receptors and may be useful in treating the symptoms of cognitive decline in an elderly patient.

Disorders of cognition are generally characterized by symptoms of forgetfulness, confusion, memory loss, attentional deficits and/or, in some cases, affective disturbances. These symptoms may arise as a result of the general aging process and/or from organic brain disease, cerebrovascular disease, head injury or developmental or genetic defects.

The general decrease in cognitive function which accompanies the aging process is well accepted. The same phenomenon has been observed and documented in many lower mammals, including those routinely employed in pharmacological testing programs for screening and predicting usefulness for particular drugs in higher animals, including humans.

Although disorders of cognition often accompany the general aging process, presenile and senile primary degenerative dementia are the most common accepted causes of mental deterioration in the elderly. It has been estimated that at least ten percent of persons over 60 years of age will eventually suffer severe mental deterioration. A much larger number will experience cognitive decline of sufficient severity to impede their activities.

Many of the symptoms of cognitive disorders, especially impaired memory, are associated with decreased acetylcholine synthesis and the impairment of cholinoreceptive neurons. In the hippocampus and cerebral cortex of patients suffering from primary degenerative dementia for example, the level of enzyme choline acetyltransferase (CAT) can be reduced as much as ninety percent (see Davies, P., et al, The Lancet, 2, page 1403 (1976); Perry, E. K., et al, Journal of Neurological Sciences, 34, pages 247-265 (1977); and White, P., et al, The Lancet, 1, pages 668-670 (1977)).

Since CAT catalyzes the synthesis of acetylcholine from its precursors choline and acetyl coenzyme A, the loss of CAT reflects the loss of cholinergic or acetylcholine-releasing nerve endings in the hippocampus and cerebral cortex. There is abundant evidence that cholinergic terminals in the hippocampus are critically important for memory formation.

The cholinergic hypothesis suggest that drugs which restore acetylcholine levels or cholinergic function (i.e., cholinomimetic) are effective in correcting this deficit in neurotransmitter chemical and provide treatment of the memory impairment symptom of cerebral insufficiency. Considerable biochemical, pharmacological, and electrophysiological evidence supports the hypothesis that deficits in the cholinergic system underlie geriatric cognitive dysfunction (Peterson, C. and Gibson, G. E., Neurobiology of Aging, 4, pages 25-30 (1983)).

Aged humans and nonhuman primates with decreased cognition show improved memory when they are treated, for example, with acetylcholinesterase inhibitors such as physostigmine. These agents increase the available supply of synaptic acetylcholine by inhibiting its hydrolysis.

Aminopyridines such as 3,4-diaminopyridine ameliorate age-related cognitive deficits by increasing the release of acetylcholine from presynaptic nerve terminals, thus increasing synaptic acetylcholine (see Davis, H. P., et al, Experimental Aging Research, 9, pages 211-214 (1983)).

It has been known for some time that the natural alkaloid, muscarine, has the ability to act relatively selectively at autonomic effector cells to produce qualitatively the same effect as acetylcholine. Two other agents, pilocarpine and oxotremorine, have the same principal sites of action as muscarine and acetylcholine and are thus classified as having "muscarinic" action.

A series of imidazole derivatives of the formula

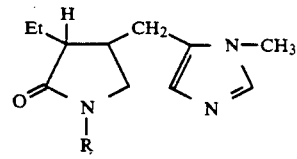

wherein R is a member selected from the group consisting of hydrogen, alkyl, aryl and aralkyl useful as anti-glaucoma agents is disclosed in U.S. Pat. No. 3,470,197.

A series of imidazole derivatives of the formula

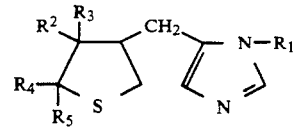

wherein
$R_1$ is $(C_{1-4})$alkyl,
$R_2$ and $R_3$ independently are hydrogen or $(C_{1-4})$alkyl,
$R_4$ and $R_5$ together are =O, =S, or =NR, wherein R is mono- or di$(C_{1-4})$alkylcarbamoyloxy, or
$R_4$ is hydrogen and
$R_5$ is hydrogen, hydroxy or —OR$^1$, wherein $R^1$ is $(C_{1-4})$alkyl or mono- or di$(C_{1-4})$ alkylcarbamoyl useful as presynaptic muscarinic antagonists or postsynaptic muscarinic agonists is disclosed in United Kingdom Patent Application GB 2,200,910A.

Borne, R. F., et al (Journal of Medicinal Chemistry, 16, pages 245-247 (1973)) disclosed various analogs of pilocarpine. In one series the lactone ring was replaced with a cyclopentanone ring and the imidazole ring replaced with 2-, or 4-pyridyl. In the other series the lactone ring was retained and the imidazole ring was replaced with 2-, or 4-pyridyl; 4-pyrimidyl; or 2-pyrazinyl. Only the derivative in which the lactone ring was retained and the imidazole ring replaced with a 4-pyrimidyl ring possessed muscarinic activity.

However, none of the compounds disclosed in the aforementioned references suggest the combination of structural variations of the compounds of the present invention described hereinafter.

It is well known that the cholinergic hypothesis suggests that cholinomimetics, including muscarinic agents, may have potential in treating senile cognitive decline (SCD). However, the multiple development issues associated with cholinomimetics, including, for example, poor bioavailability, short duration of action, and especially parasympathetic side effects, have diminished hopes of adequate therapy with this class of agents.

The novel substituted hetero-cyclopentanones and cyclopentenones and derivatives thereof of the present invention which are related to pilocarpine may have high affinity for the muscarinic receptor and thus are expected to be useful in the treatment of the symptoms of cognitive decline in an elderly patient including Alzheimer's disease.

SUMMARY OF THE INVENTION

Accordingly, the present invention is a compound of Formula I

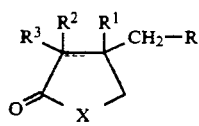

wherein X is oxygen, sulfur, or —N—R$^4$ wherein R$^4$ is hydrogen or alkyl of from one to ten carbon atoms; R is selected from the group consisting of

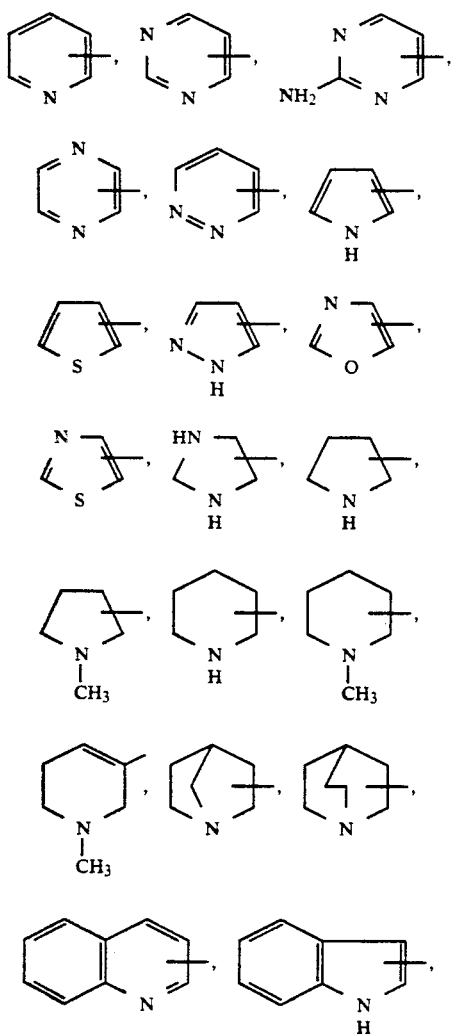

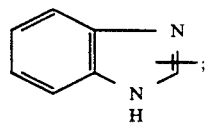

and $R^1$, $R^2$, and $R^3$ are each independently hydrogen, alkyl of from one to ten carbon atoms, alkynyl of from two to ten carbon atoms or aryl;  represents a single or double bond with the proviso that when  represents a double bond $R^1$ and $R^2$ are absent; or a pharmaceutically acceptable acid addition salt thereof, excluding a compound wherein X is oxygen; R is selected from the group consisting of

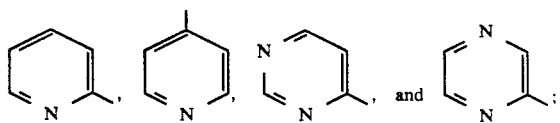

$R^1$ is hydrogen; $R^2$ is hydrogen; $R^3$ is alkyl of from one to ten carbon atoms; and  represents a single bond.

As centrally acting muscarinic agents, the compounds of Formula I are useful as analgesic agents for the treatment of pain in mammals including man, as sleep aids, and as agents for treating the symptoms of senile dementia, Alzheimer's disease, Huntington's chorea, tardive dyskinesia, hyperkinesia, mania or similar conditions of cerebral insufficiency characterized by decreased cerebral acetylcholine production or release.

A still further embodiment of the present invention is a pharmaceutical composition for administering an effective amount of a compound of Formula I in unit dosage form in the treatment methods mentioned above.

Finally, the present invention is directed to methods for production of a compound of Formula I.

DETAILED DESCRIPTION OF THE INVENTION

In the compounds of Formula I, the term "alkyl" means a straight or branched hydrocarbon radical having from one to ten carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl, and the like.

The term "alkynyl" means a straight or branched triple bonded unsaturated hydrocarbon radical having from two to ten carbon atoms and includes, for example, ethynyl, 2-propynyl, 1-butynyl, 2-butynyl, 3-butynyl, 1-pentynyl, 3-pentynyl, 1-hexynyl, 2-hexynyl, 3-hexynyl, 3-heptynyl, 1-octynyl, 2-octynyl, 1-nonynyl, 2-nonynyl, 3-nonynyl, 4-nonynyl, 1-decynyl, 2-decynyl, and the like.

The term "alkoxy" means alkyl-O- of from one to ten carbon atoms as defined above for "alkyl".

The term "thioalkoxy" means alkyl-S- of from one to ten carbon atoms as defined above for "alkyl".

The term "aryl" means an aromatic radical which is a phenyl group or phenyl group substituted by one to four substituents selected from alkyl, alkoxy, thioalkoxy, halogen or trifluoromethyl such as, for example, benzyl, phenethyl, and the like.

"Halogen" is fluorine, chlorine, bromine, or iodine.

Pharmaceutically acceptable acid addition salts of the compounds of Formula I include salts derived from nontoxic inorganic acids, such as hydrochloric, nitric, phosphoric, sulfuric, hydrobromic, hydriodic, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, capryl-ate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge, S. M., et al, "Pharmaceutical Salts," *Journal of Pharmaceutical Science*, Vol. 66, pages 1-19 (1977)).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free bases for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess asymmetric carbon atoms (optical centers); the racemates as well as the individual enantiomers are intended to be encompassed within the scope of the present invention.

A preferred compound of Formula I is one wherein R is selected from the group consisting of

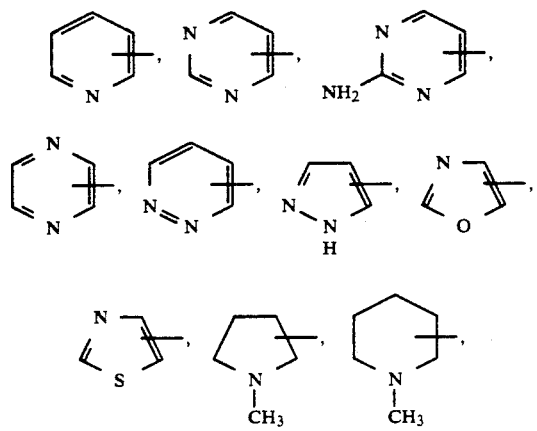

-continued

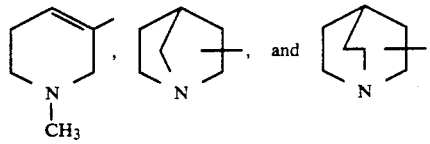

A more preferred compound of Formula I is one wherein $R^1$, $R^2$, and $R^3$ are each independently hydrogen or alkyl of from one to six carbon atoms.

Particularly valuable are:
3-Ethyldihydro-4-(4-pyrimidinylmethyl)-2(3H)-furanone;
3-Ethyldihydro-4-(3-pyridazinylmethyl)-2(3H)-furanone;
3-Ethyldihydro-4-(4-pyridazinylmethyl)-2(3H)-furanone;
3-Ethyldihydro-4-(4-oxazolylmethyl)-2(3H)-furanone;
3-Ethyldihydro-4-(5-oxazolylmethyl)-2(3H)-furanone;
3-Ethyldihydro-4-(5-thiazolylmethyl)-2(3H)-furanone;
3-Ethyldihydro-4-(4-thiazolylmethyl)-2(3H)-furanone;
3-Ethyldihydro-4-[(1,2,5,6-tetrahydro-1-methyl-3-pyridinyl)methyl]-2-(3H)-furanone;
4-[(1-Azabicyclo[2.2.1]hept-3-yl)methyl]-3-ethyldihydro-2-(3H)-furanone;
4-[(1-Azabicyclo[2.2.2]oct-3-yl)methyl]-3-ethyldihydro-2-(3H)-furanone;
3-Ethyldihydro-4-(2-pyridinylmethyl)-2(3H)-thiophenone;
3-Ethyldihydro-4-(4-pyridinylmethyl)-2(3H)-thiophenone;
3-Ethyldihydro-4-(5-pyrimidinylmethyl)-2(3H)-thiophenone;
3-Ethyldihydro-4-(4-pyrimidinylmethyl)-2(3H)-thiophenone;
3-Ethyldihydro-4-(3-pyridazinylmethyl)-2(3H)-thiophenone;
3-Ethyldihydro-4-(4-pyridazinylmethyl)-2(3H)-thiophenone;
3-Ethyldihydro-4-(4-oxazolylmethyl)-2(3H)-thiophenone;
3-Ethyldihydro-4-(5-oxazolylmethyl)-2(3H)-thiophenone;
3-Ethyldihydro-4-(5-thiazolylmethyl)-2(3H)-thiophenone;
3-Ethyldihydro-4-(4-thiazolylmethyl)-2(3H)-thiophenone;
3-Ethyldihydro-4-[(1,2,5,6-tetrahydro-1-methyl-3-pyridinyl(methyl]-2-(3H)-thiophenone;
4-[(1-Azabicyclo[2.2.1πhept-3-yl)methyl]-3-ethyldihydro-2(3H)-thiophenone;
4-[(1-Azabicyclo[2.2.2]oct-3-yl)methyl]-3-ethyldihydro-2(3H)-thiophenone;
3-Ethyl-4-(2-pyridinylmethyl)-2-pyrrolidinone;
3-Ethyl-4-(4-pyridinylmethyl)-2-pyrrolidinone;
3-Ethyl-4-(5-pyrimidinylmethyl)-2-pyrrolidinone;
3-Ethyl-4-(4-pyrimidinylmethyl)-2-pyrrolidinone;
3-Ethyl-4-(3-pyridazinylmethyl)-2-pyrrolidinone;
3-Ethyl-4-(4-pyridazinylmethyl)-2-pyrrolidinone;
3-Ethyl-4-(4-oxazolylmethyl)-2-pyrrolidinone;
3-Ethyl-4-(5-oxazolylmethyl)-2-pyrrolidinone;
3-Ethyl-4-(5-thiazolylmethyl)-2-pyrrolidinone;

3-Ethyl-4-(4-thiazolylmethyl)-2-pyrrolidinone;
3-Ethyl-4-(1,2,5,6-tetrahydro-1-methyl-3pyridinyl)-methyl]-2-pyrrolidinone;
4-[(1-Azabicyclo[2.2.1]hept-3-yl)methyl]-3-ethyl-2-pyrrolidinone;
4-[(1-Azabicyclo[2.2.2]oct-3-yl)methyl]-3-ethyl-2-pyrrolidinone;
3-Ethyl-1-methyl-4-(2-pyridinylmethyl)-2-pyrrolidinone;
3-Ethyl-1-methyl-4-(4-pyridinylmethyl)-2-pyrrolidinone;
3-Ethyl-1-methyl-4-(5-pyrimidinylmethyl)-2-pyrrolidinone;
3-Ethyl-1-methyl-4-(4-pyrimidinylmethyl)-2-pyrrolidinone;
3-Ethyl-1-methyl-4-(3-pyridazinylmethyl)-2-pyrrolidinone;
3-Ethyl-1-methyl-4-(4-pyridazinylmethyl)-2-pyrrolidinone;
3-Ethyl-1-methyl-4-(4-oxazolylmethyl)-2-pyrrolidinone;
3-Ethyl-1-methyl-4-(5-oxazolylmethyl)-2-pyrrolidinone;
3-Ethyl-1-methyl-4-(5-thiazolylmethyl)-2-pyrrolidinone;
3-Ethyl-1-methyl-4-(4-thiazolylmethyl)-2-pyrrolidinone;
3-Ethyl-1-methyl-4-[(1,2,5,6-tetrahydro-1-methyl-3pyridinyl)methyl]-2-pyrrolidinone;
4-[(1-Azabicyclo[2.2.1]hept-3-yl)methyl]-3-ethyl-1-methyl-2-pyrrolidinone;
4-[(1-Azabicyclo[2.2.2]oct-3-yl)methyl]-3-ethyl-1-methyl-2-pyrrolidinone;
1,3-Diethyl-4-(2-pyridinylmethyl)-2-pyrrolidinone;
1,3-Diethyl-4-(4-pyrimidinylmethyl)-2-pyrrolidinone;
1,3-Diethyl-4-(5-pyrimidinylmethyl)-2-pyrrolidinone;
1,3-Diethyl-4-(4-pyrimidinylmethyl)-2-pyrrolidinone;
1,3-Diethyl-4-(3-pyridazinylmethyl)-2-pyrrolidinone;
1,3-Diethyl-4-(4-pyridazinylmethyl)-2-pyrrolidinone;
1,3-Diethyl-4-(4-oxazolylmethyl)-2-pyrrolidinone;
1,3-Diethyl-4-(5-oxazolylmethyl)-2-pyrrolidinone;
1,3-Diethyl-4-(5-thiazolylmethyl)-2-pyrrolidinone;
1,3-Diethyl-4-(4-thiazolylmethyl)-2-pyrrolidinone;
1,3-Diethyl-4-[(1,2,5,6-tetrahydro-1-methyl-3pyridinyl)methyl]-2-pyrrolidinone;
4-[(1-Azabicyclo[2.2.1]hept-3-yl)methyl]-1,3-diethyl-2-pyrrolidinone; and
4-[(1-Azabicyclo[2.2.1]oct-3-yl)methyl]-1,3-diethyl-2-pyrrolidinone; or
a pharmaceutically acceptable salt thereof.

The compounds of Formula I are valuable centrally acting muscarinic agents. The biological activity of compounds of the present invention can be evaluated using a number of tests. The activity of compounds of the present invention as central muscarinic binding site agonists and antagonists can be measured. Thus, in the Receptor [³H]Quinuclidinyl Benzilate Binding Assay (RQNB), described more fully by Watson, M., et al, *Journal of Pharmacology and Experimental Therapeutics*, 237, pages 411 to 418 (1986), rat cerebral cortex tissue is treated with radiolabeled quinuclidinyl benzilate, a known muscarinic binding site antagonist. The concentration of test compound required to inhibit 50% of the binding of this muscarinic antagonist is then determined. This procedure allows a determination of the affinity of the test compounds for the central muscarinic antagonist site. Similarly in the Receptor [³H]Cis-methyldioxalane Assay (RCMD), described more fully by Vickroy, T. W., et al, *Journal of Pharmacology and Experimental Therapeutics*, 229, pages 747 to 755 (1984), rat cerebral cortex tissue is treated with radiolabeled cis-methyldioxalane, a known muscarinic binding site agonist. The concentration of test compound required to inhibit 50% of the binding of this muscarinic against is then determined. This procedure allows a determination of the affinity of the test compound for the central muscarinic agonist site.

In the Muscarinic Induced Inositol Phosphate Accumulation Assay (MIPA) human SK-N-SH cells bearing muscarinic binding sites are incubated with the test compound. The production of inositol phosphates is then measured. Stimulation of inositol phosphate turnover reflects the degree of muscarinic agonist activity of the test compound. The concentration of test compound required to produce a response 50% of the maximum is then determined.

A compound of Formula Ia

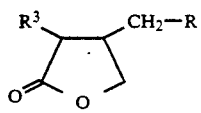

wherein R is selected from the group consisting of

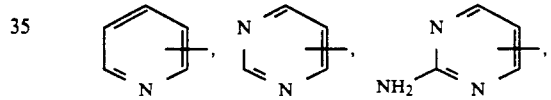

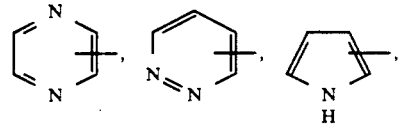

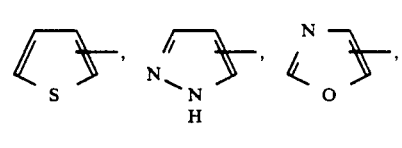

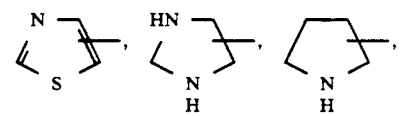

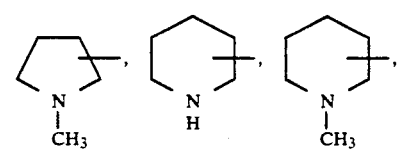

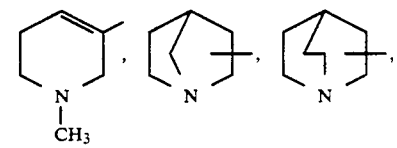

[Structures: quinoline, indole-NH, and benzimidazole-like fragment]

and R³ is hydrogen, alkyl of from one to ten carbon atoms, alkynyl of from two to ten carbon atoms or aryl; or a pharmaceutically acceptable acid addition salt thereof, may be prepared by reacting a compound of Formula II

[Structure II: γ-butyrolactone with R³ substituent, α,β-unsaturated]   II wherein R³ is as defined above with a compound of Formula III R—CH₂Na    III wherein R is as defined above to give a compound of Formula Ia.

A compound of Formula Ib

[Structure Ib: γ-butyrolactone with R² and R³ on α-carbon, CH₂—R on β-carbon]   Ib wherein R² and R³ are alkyl of from one to ten carbon atoms, alkynyl of from two to ten carbon atoms or aryl, and R is as defined above may be prepared from a compound of Formula Ia and a compound of Formula IV

R²X    IV wherein R² is alkyl of from one to ten carbon atoms and X is halogen in the presence of a base such as, for example, lithium diisopropylamide, and the like to give a compound of Formula Ib.

A compound of Formula Ic

[Structure Ic: γ-thiobutyrolactone with R³ and CH₂—R]   Ic wherein R³ is hydrogen or alkyl of from one to ten carbon atoms, alkynyl of from two to ten carbon atoms or aryl, and R is as defined above may be prepared from a compound of Formula Ia and a thiolating reagent such as, for example, potassium thioacetate, to give a compound of Formula Ib.

A compound of Formula Id

[Structure Id: γ-lactam with R³, CH₂—R, and N—R⁴]   Id wherein R³ and R⁴ are hydrogen, alkyl from one to ten carbon atoms, alkynyl of from two to ten carbon atoms or aryl, and R is as defined above may be prepared from a compound of Formula Ia and a compound of Formula V

R⁴NH₂    V wherein R⁴ is as defined above to give a compound of Formula Id.

A compound of Formula Ie

[Structure Ie: γ-thiobutyrolactone with R², R³, CH₂—R]   Ie wherein R² and R³ are alkyl of from one to ten carbon atoms, alkynyl of from two to ten carbon atoms or aryl, and R is as defined above may be prepared from a compound of Formula Ib and a thiolating reagent such as, for example, potassium thioacetate, and the like to give a compound of Formula Ie.

A compound of Formula If

[Structure If: γ-lactam with R², R³, CH₂—R, N—R⁴]   If wherein R² and R³ are alkyl of from one to ten carbon atoms, alkynyl of from two to ten carbon atoms or aryl, and R and R⁴ are as defined above may be prepared from a compound of Formula Ib and a compound of Formula V to give a compound of Formula If.

A compound of Formula Ig

[Structure Ig: α,β-unsaturated γ-butyrolactone with R³ and CH₂—R]   Ig wherein R³ is hydrogen, alkyl of from one to ten carbon atoms, alkynyl of from two to ten carbon atoms or aryl, and R is as defined above may be prepared by reacting a compound of Formula Ia with phenylselenenyl chloride and a base such as, for example, lithium diisopropylamide to give the intermediate phenylselenyl derivative which is subsequently oxidized with an oxidizing reagent such as, for example, sodium methaperiodate, and the like to give a compound of Formula Ig.

A compound of Formula Ih

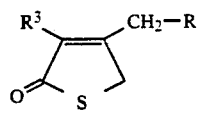

wherein $R^3$ is hydrogen, alkyl of from one to ten carbon atoms, alkynyl of from two to ten carbon atoms or aryl, and R is as defined above may be prepared from a compound of Formula Ig and a thiolating reagent such as, for example, potassium thioacetate, and the like to give a compound of Formula Ih.

A compound of Formula Ii

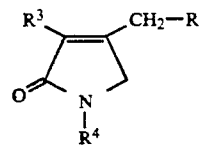

wherein $R^3$ and $R^4$ are hydrogen, alkyl of from one to ten carbon atoms, alkynyl of from two to ten carbon atoms or aryl, and R is as defined above may be prepared from a compound of Formula Ig and a compound of Formula V to give a compound of Formula Ii.

A compound of Formula Ij

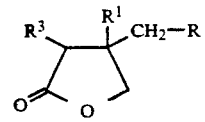

wherein $R^3$ is hydrogen, alkyl of from one to ten carbon atoms, alkynyl of from two to ten carbon atoms or aryl, $R^1$ is alkyl of from one to ten carbon atoms, alkynyl of from two to ten carbon atoms or aryl, and R is as defined above may be prepared from a compound of Formula Ig and a compound of Formula VI $(R^1)_2CuLi$   VI wherein $R^1$ is as defined above to give a compound of Formula Ij.

A compound of Formula Ik

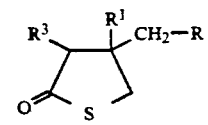

wherein $R^3$ is hydrogen, alkyl of from one to ten carbon atoms, alkynyl of from two to ten carbon atoms or alkyl, $R^1$ is alkyl of from one to ten carbon atoms, alkynyl of from two to ten carbon atoms or aryl, and R is as defined above may be prepared from a compound of Formula Ij and a thiolating reagent such as, for example, potassium thioacetate, and the like to give a compound of Formula Ik.

A compound of Formula Il

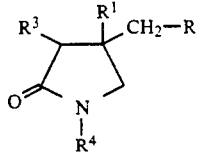

wherein $R^1$ is alkyl of from one to ten carbon atoms, alkynyl of from two to ten carbon atoms or aryl, $R^3$ and $R^4$ are hydrogen or alkyl of from one to ten carbon atoms, alkynyl of from two to ten carbon atoms or aryl, and R is as defined above may be prepared from a compound of Formula Ij and a compound of Formula V to give a compound of Formula Il.

A compound of Formula Im

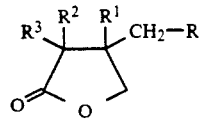

wherein $R^1$ is alkyl of from one to ten carbon atoms, alkynyl of from two to ten carbon atoms or aryl, $R^2$ and $R^3$ are hydrogen, alkyl of from one to ten carbon atoms, alkynyl of from two to ten carbon atoms or aryl, and R is as defined above may be prepared from a compound of Formula Ij and a compound of Formula V in the presence of a base such as, for example, lithium diisopropylamide, and the like to give a compound of Formula Im.

A compound of Formula In

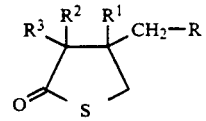

wherein $R^1$ is alkyl of from one to ten carbon atoms, alkynyl of from two to ten carbon atoms or aryl, $R^2$ and $R^3$ are hydrogen, alkyl of from one to ten carbon atoms, alkynyl of from two to ten carbon atoms or aryl, and R is as defined above may be prepared from a compound of Formula Im and a thiolating reagent such as, for example, potassium thioacetate, and the like to give a compound of Formula In.

A compound of Formula Io

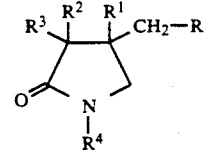

wherein $R^1$ is alkyl of from one to ten carbon atoms, alkynyl of from two to ten carbon atoms or aryl, $R^2$ and $R^3$ are hydrogen, alkyl of from one to ten carbon atoms, alkynyl of from two to ten carbon atoms or aryl, and R is as defined above may be prepared from a compound of Formula Im and a compound of Formula V to give a compound of Formula Io.

Compounds of Formula II, Formula III, Formula IV, Formula V, and Formula VI are either known or capable of being prepared by methods known in the art.

The compounds of the present invention can be prepared and administered in a wide variety of oral and parenteral dosage forms. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.7 to 7000 mg depending upon the particular application and the potency of the active component. The composition can, if desired, also contain other compatible therapeutic agents.

In therapeutic use as centrally active muscarinic agents the compounds utilized in the pharmaceutical method of this invention are administered at the initial dosage of about 0.01 to about 100 mg per kilogram daily. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventor's preferred methods for preparing the compounds of the invention.

EXAMPLE 1

3-Ethyldihydro-4-(3-pyridazinylmethyl)-2-(3H)-furanone

STEP A: Preparation of 3-Ethyl-2(5H)-furanone

A mixture of γ-butyrolactone (1 mol) and tris(dimethylamino)methane (1.5 mol) is stirred under dry nitrogen at 75° C. for 2 days to give 3-[(dimethylamino)methylene]dihydro-2(3H)-furanone. A solution containing 3-[(dimethylamino)methylene]dihydro-2(3H)-furanone (1 mol), n-butanethiol (1.1 mol) and para-toluenesulfonic acid (1 mol) in benzene is heated at reflux overnight to give upon aqueous work-up 3-[(butylthio)methylene]dihydro-2(3H)-furanone. After a solution of 3-[(butylthio)methylene]dihydro-2(3H)-furanone (1 mol) in anhydrous diethyl ether is added to a solution of lithium di-n-butylcuprate (1.1 mol) in diethyl ether at −78° C., the resulting mixture is stirred at −78° C. for an additional 0.5 hours and then quenched with methanol. Work-up affords 3-ethylidenedihydro-2(3H)-furanone. Freshly prepared W-2 Raney nickel (about 3 parts) is deactivated by refluxing in benzene for 1 hour, whereupon 3-ethylidenedihydro-2(3H)-furanone is added and the mixture is heated at reflux under nitrogen for 24-48 hours; the reaction is monitored by thin layer chromatography. After complete washing of the Raney nickel with hot benzene, the title compound is obtained.

STEP B: Preparation of 3-Ethyldihydro-4-(3-pyridazinylmethyl)-2(3H-furanone)

A solution of 4.7 g (0.05 mol) of 3-methylpyridazine in 50 mL of diethyl ether is added to a suspension of sodium amide (2.0 g, 0.05 mol) in 50 mL of diethyl ether over a period of 30 minutes. The mixture is refluxed 45 minutes, cooled to room temperature, and a solution of 5.6 g (0.05 mol) of 3-ethyl-2(5H)-furanone in 50 mL of diethyl ether is added. The mixture is stirred overnight at room temperature, refluxed an additional 2 hours, and cooled. The reaction is quenched by the addition of 50 mL of water followed by 200 mL of dilute (1:1) hydrochloric acid and the reaction mixture extracted with diethyl ether. The acidic layer is rendered alkaline with sodium carbonate and extracted with chloroform. The chloroform extracts are dried (magnesium sulfate) and evaporated. Unreacted pyridazine is removed by distillation at reduced pressure. The residue is purified by silica gel chromatography to give the title compound.

EXAMPLE 2

3-Ethyl-4-(3-pyridazinylmethyl)-2-pyrrolidinone

Three grams (0.0145 mol) of 3-ethyl-4-(3-pyridazinylmethyl)-2-pyrrolidinone (Example 1) is suspended in 25 mL of aqueous ammonium hydroxide solution (28%) and the mixture is stirred at room temperature. Stirring is continued for 2 hours. The heavy white suspension is filtered and the product recrystallized from a minimum amount of aqueous ammonium hydroxide solution (28%) to give the title compound.

EXAMPLE 3

3-Ethyldihydro-4-(3-pyridazinylmethyl)-2-(3H)-thiophenone

Potassium thioacetate (3.3 g, 0.029 mol) and 3.0 g (0.0145 mol) of 3-ethyl-4-(3-pyridazinylmethyl)-2-pyrrolidinone (Example 1) are stirred for 6 hours at 150° C. in 50 mL of dimethylformamide. After cooling and evaporating the solvent, the residue is dissolved in 95% methylene chloride/methanol, washed twice with saturated sodium bicarbonate solution and once with water. After drying the organic phase with sodium sulphate, the mixture is filtered and concentrated by evaporation. The product is purified by chromatography in silica gel to give the title compound.

I claim:

1. A compound of Formula I

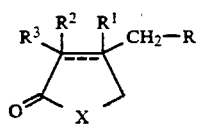

wherein X is oxygen, sulfur, or —N—R$^4$ wherein R$^4$ is hydrogen or alkyl of from one to ten carbon atoms; R is selected from the group consisting of

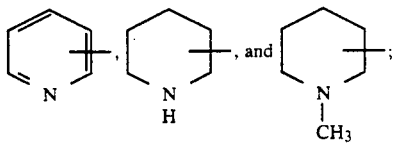

R$^1$, R$^2$, and R$^3$ are each independently hydrogen, alkyl of from one to ten carbon atoms, alkynyl of from two to ten carbon atoms or, phenyl or phenyl substituted by one to four substituents selected from C$_1$-C$_{10}$ alkyl, alkoxy, C$_1$-C$_{10}$, halogen or trifluoromethyl; ------- represents a single or double bond with the proviso that when ------- represents a double bond R$^1$ and R$^2$ are absent; or a pharmaceutically acceptable acid addition salt thereof, excluding a compound wherein X is oxygen; R is selected from the group consisting of

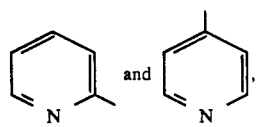

R$^1$ is hydrogen; R$^2$ is hydrogen; R$^3$ is alkyl of from one to ten carbon atoms; and ------- represents a single bond.

2. A compound according to claim 1, in which R is selected from the group consisting of

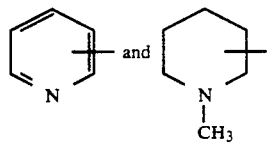

3. A compound according to claim 2, in which R$^1$, R$^2$, and R$^3$ are each independently hydrogen or alkyl of from one to six carbon atoms.

4. A compound according to claim 3 selected from the group consisting of:
 3-Ethyldihydro-4-(2-pyridinylmethyl)-2(3H)-thiophenone;
 3-Ethyldihydro-4-(4-pyridinylmethyl)-2(3H)-thiophenone;
 3-Ethyl-4-(2-pyridinylmethyl)-2-pyrrolidinone;
 3-Ethyl-4-(4-pyridinylmethyl)-2-pyrrolidinone;
 3-Ethyl-1-methyl-4-(2-pyridinylmethyl)-2-pyrrolidinone;
 3-Ethyl-1-methyl-4-(4-pyridinylmethyl)-2-pyrrolidinone;
 1,3-Diethyl-4-(2-pyridinylmethyl-2-pyrrolidinone; and
 1,3-Diethyl-4-(4-pyridinylmethyl)-2-pyrrolidinone.

5. A method of treating the symptoms of cognitive decline in an elderly patient comprising administering to a patient suffering therefrom a cholinergically effective amount of a compound according to claim 1.

6. A pharmaceutical composition for the treatment of the symptoms of cognitive decline in an elderly patient comprising administering to a patient suffering therefrom a cholinergically effective amount of a compound according to claim 5 in combination with a pharmaceutically acceptable carrier.

* * * * *

UNITED STATES PATENT AND TRADEMARK OFFICE
CERTIFICATE OF CORRECTION

PATENT NO. : 5,066,663
DATED : November 19, 1991
INVENTOR(S) : HOBBS, S. H.

It is certified that error appears in the above-identified patent and that said Letters Patent is hereby corrected as shown below:

In column 16, line 12, insert at end of line $--C_1-C_{10}--$.

In column 16, line 13, insert after $C_{10}$ --alkylthio--.

Signed and Sealed this

Thirtieth Day of March, 1993

Attest:

STEPHEN G. KUNIN

Attesting Officer

Acting Commissioner of Patents and Trademarks